United States Patent [19]

Fertig et al.

[11] Patent Number: 5,095,900
[45] Date of Patent: Mar. 17, 1992

[54] RESPIRATION MONITOR

[75] Inventors: Glenn H. Fertig, Natrona Heights; William Nelko, Ambridge; Richard F. Abt, Pittsburgh, all of Pa.

[73] Assignee: Mine Safety Appliances Company, Pittsburgh, Pa.

[21] Appl. No.: 644,017

[22] Filed: Jan. 22, 1991

[51] Int. Cl.[5] .................................................. A61B 5/08
[52] U.S. Cl. ................................ 128/207.14; 128/716; 128/719; 128/205.23
[58] Field of Search ................ 128/207.14, 207.15, 128/205.23, 202.22, 719, 716

[56] References Cited

U.S. PATENT DOCUMENTS

| | | | |
|---|---|---|---|
| 4,485,822 | 12/1984 | O'Connor et al. | 128/719 |
| 4,549,553 | 10/1985 | Hochberg | 128/719 |
| 4,648,396 | 3/1987 | Raemer | 128/719 |

Primary Examiner—Edgar S. Burr
Assistant Examiner—Aaron J. Lewis

[57] ABSTRACT

A respiration monitor that indicates respiration or loss of respiration by detecting carbon dioxide in expired air in an endotracheal tube comprises a tubular member adapted to receive respired air from an endotracheal tube and having diametrically opposed planar windows substantially transparent to infrared radiation; an infrared analyzer comprising a source means for producing an unmodulated beam of infrared radiation passing through the planar windows and respired air, and a solid state detector means to receive infrared radiation after passage through said windows and respired air and to generate an output signal in response to the presence of $CO_2$ in respired air, means for detecting the time between signals generated by said detector, and alarm means responsive to a predetermined delay between said signals.

6 Claims, 2 Drawing Sheets

RESPIRATION MONITOR

FIELD OF THE INVENTION

This invention relates to a respiration monitor and more particularly to a monitor responsive to $CO_2$ in respired air in an endotracheal tube.

BACKGROUND OF THE INVENTION

In surgical and field emergency situations it is commonly necessary to introduce an endotracheal tube to a patient to aid or permit respiration. It is necessary to determine that the tube has been properly introduced into the trachea and not the esophagus. In surgical settings, the quantitative measurement of carbon dioxide by capnometers during the respiratory cycle has been used to confirm proper tube placement. P. K. Birmingham et al., "Esophageal Intubation", Anesth. Analy, 1986, 65, 865–91. Capnometers are not considered suitable for emergency field use because they are expensive and not reliable under extreme ambient conditions or when subjected to rough handling.

Colorimetric indicators responsive to $CO_2$ have been connected to endotracheal tubes to provide a qualitative indication of $CO_2$ in the tube that indicates the correct location of the tube (see U.S. Pat. Nos. 4,691,701 and 4,728,499). However, these devices are single patient use, subject to the user's color perception and must be directly observed at all times to verify respiration.

Fertig et al., U.S. Pat. No. 4,595,016 discloses an Apnea monitor in which a continuous breath sample is drawn through the cell of an infrared analyzer comprising a capacitor microphone detector responsive to $CO_2$ in exhaled breath. The capacitor microphone generates a signal each time it detects an exhaled breath. When a timer senses an extended delay between signals, an alarm sounds indicating the presence of an Apnea condition. Capacitor microphone detectors are vibration sensitive and therefore subject to damage by field use handling.

SUMMARY OF THE INVENTION

It is an object of this invention to provide a simple, rugged respiration monitor that indicates respiration or loss of respiration by detecting carbon dioxide in expired air in an endotracheal tube. The respiration monitor of this invention for attachment to an endotracheal tube comprises a tubular member adapted to receive respired air from an endotracheal tube and having diametrically opposed planar windows substantially transparent to infrared radiation; an infrared analyzer comprising a source means for producing an unmodulated beam of infrared radiation passing through the planar windows and respired air, and a solid state detector means to receive infrared radiation after passage through said windows and respired air and to generate an output signal in response to the presence of $CO_2$ in respired air,
means for detecting the time between signals generated by said detector,
and alarm means responsive to a predetermined delay between said signals.

DESCRIPTION OF THE PREFERRED EMBODIMENT

Figure 1:
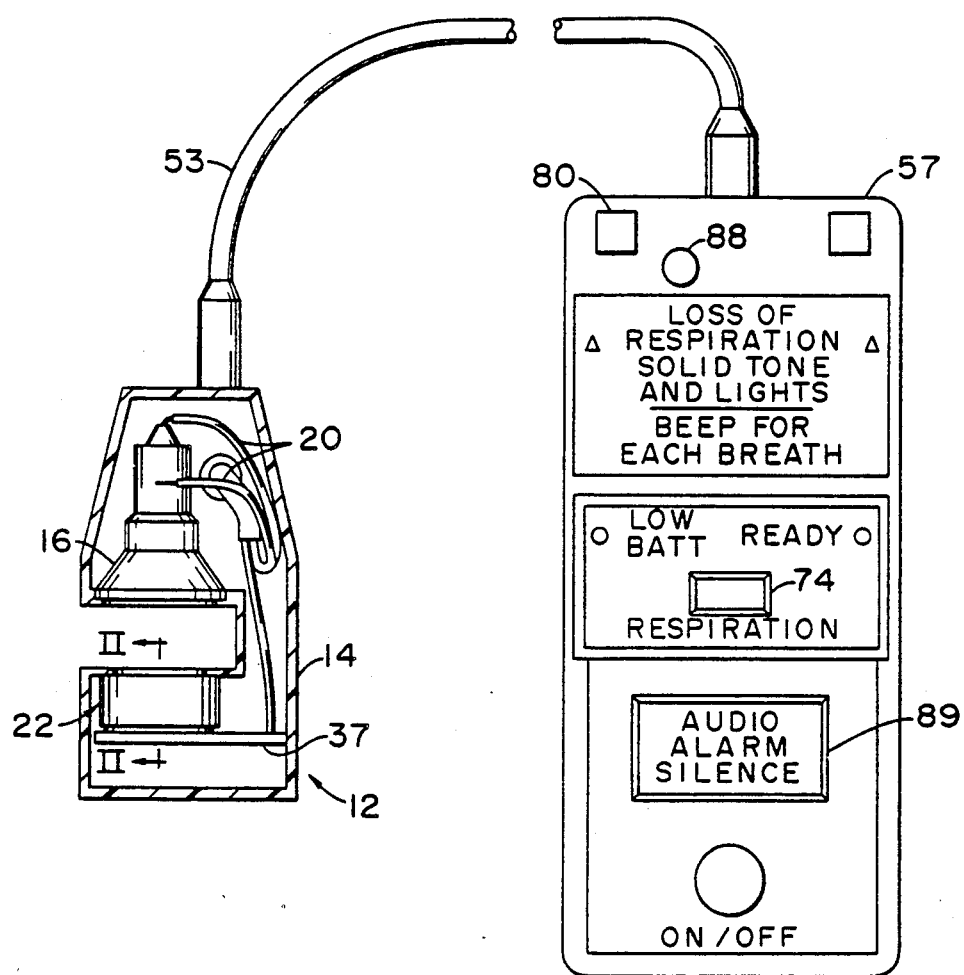
FIG. 1 is a partly-broken away view of the sensor assembly and indicator case of this invention.
Figure 2:
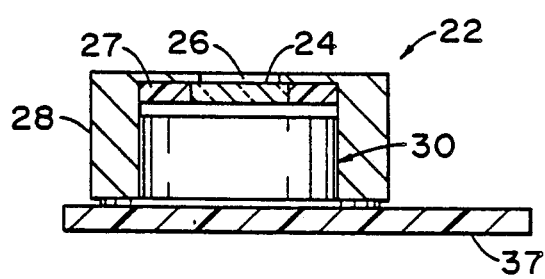
FIG. 2 is a cross-sectional view of the detector assembly of FIG. 1 taken on line II—II.
Figure 3:
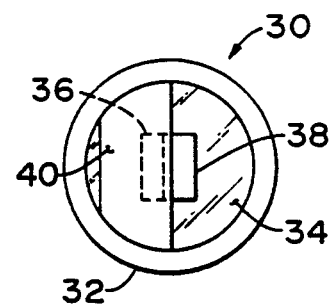
FIG. 3 is a top view of the detector of the detector assembly of FIG. 2.

With reference to FIGS. 1–4, a tubular adapter 2 has a generally rectangular portion 4 having diametrically opposed planar windows 6 and 8. An end of the adapter 9 is sized to fit a standard endotracheal tube. The other end of the adapter 10 is sized to fit an air oxygen supply tube or, in cases where air or oxygen is not supplied to the patient, is open to the ambient atmosphere. Respired air, or other breathing gas, flows to and from through the adapter. The portion of the adapter between the windows is in effect a sample cell for the respired air.

A sensor assembly 12 has a U-shaped housing 14 adapted to fit over the windows of the adapter 2. One leg of the housing contains an infrared source housed in a reflector 16 that is connected to a power source by leads 20. When positioned on the adapter, the infrared beam passes through windows 6 and 8 and the contained respired air. The opposing leg of the housing contains a detector assembly 22 that receives the infrared radiation that passes through the windows and respired air. The assembly comprises a dielectric bandpass interference filter 24 having an effective bandwidth of 0.2 microns and a center wavelength of 4.27 microns chosen to match the absorption characteristics of carbon dioxide in the infrared portion of the spectrum. The interference filter is mounted in optical filter mount 27 and secured adjacent opening 26 in the end wall of copper sheath 28 that fits over and tightly engages the sidewalls of infrared detector 30.

The detector 30 comprises a metal housing 32 with one end wall having an infrared transparent window 31 and a pair of matched solid state infrared sensitive elements 36 and 38 mounted on a common substrate. The detector is supported on printed circuit board 37. Solid state elements that are not vibration or shock sensitive can be used, such as, for example, pyro-electric, lead selenide and thermopile elements The preferred element is a thermopile. The detector 30 is assembled as a hermetically-sealed unit and is filled with argon gas. An argon gas fill is necessary, even though it produces less signal than a conventional nitrogen-filled detector, to obtain a sufficiently rapid response time for respiration monitoring. The preferred detector described is Dexter Corporation Model DR46 filled with argon gas and having a sapphire window.

A metal foil tape shield 40 is secured to the outer surface of the detector window and directly in front of the radiation sensitive element 36 chosen to be the reference element. The unshielded element 38 is the measuring element. It is necessary that the shield be on the outside rather than the inside surface of the window. When the shield is on the inside, large thermal differences between the reference and the measuring elements destroy the thermal match of the elements causing spurious signals.

It was expected that matched thermopile, or other solid state elements having a temperature-dependent output, mounted on a common substrate would overcome the problems associated with large step changes in temperature. However, thermal testing showed that elements with matched outputs under static conditions did not track each other under dynamic thermal conditions. Thermal gradient differences between elements were sometimes sufficient to cause a false signal, due entirely to the temperature difference between the elements, that indicated the presence of $CO_2$. Significant thermal gradients between detector elements are avoided by placing the detector 30 in the housing 32 of a metal with high thermal conductivity, such a copper. The housing serves as a heat sink to damp temperature changes and provides a uniform temperature around the detector Temperature changes resulting are preferentially further damped by thermal insulation provided by plastic housing 14.

Fogging of the windows 6 and 8 caused by moisture in the respired air may give a false indication of $CO_2$, so it is important that windows 6 and 8 be resistant to fogging. Quartz and mica windows, with or without commercial anti-fogging coatings, can be used but they are quite expensive. The now preferred window material is Eastman Kodak Estar® UDF LPD-4 film that has been exposed to light and developed. The resultant clear polyester film resists water vapor fogging down to a temperature of 0° C.

Figures 4, 5:
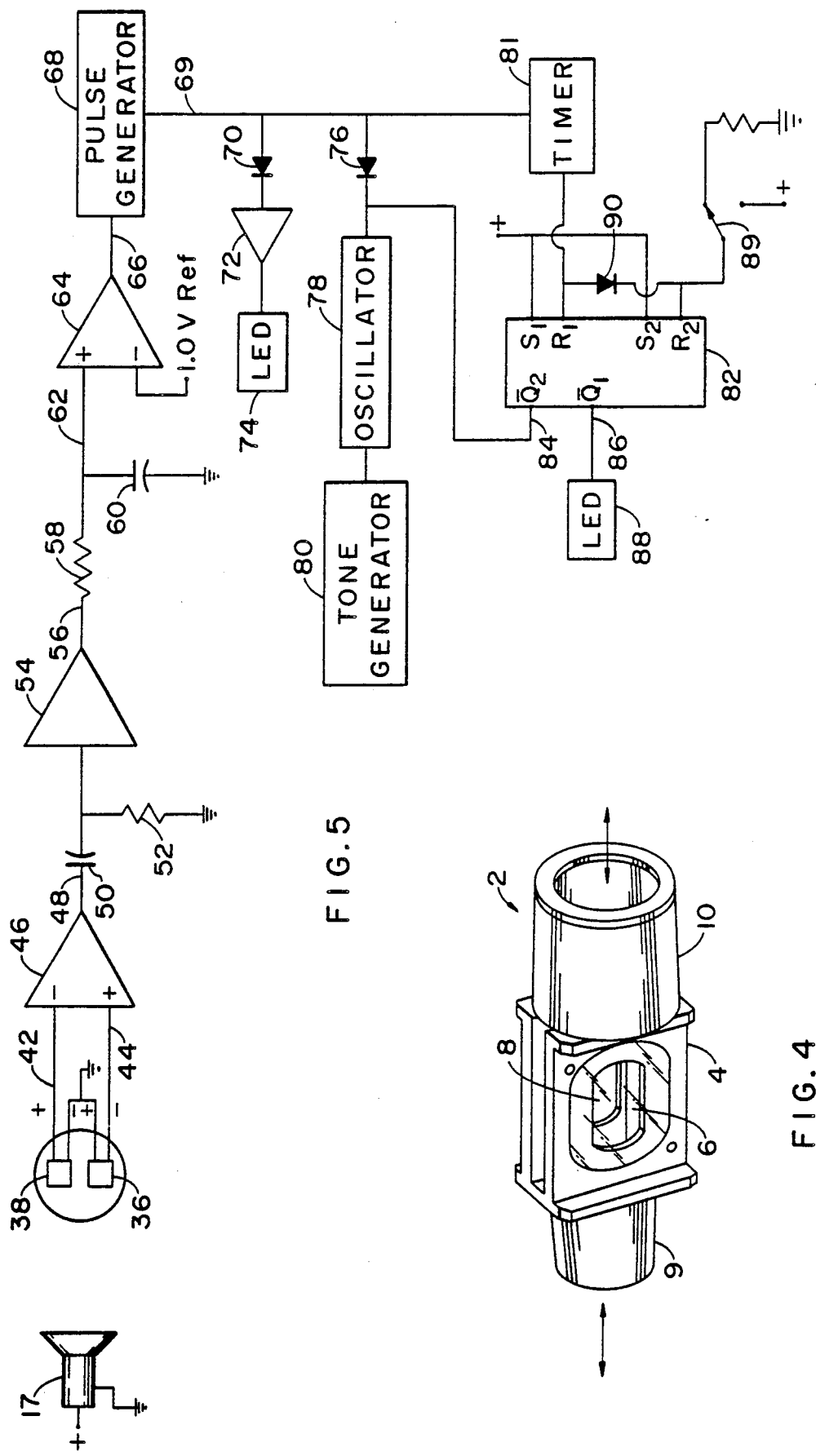
FIG. 4 is a perspective view of an airway adapter that fits in the sensor assembly of FIG. 1.
FIG. 5 is a diagram of the measuring and alarm circuits of the instrument of FIG. 1.

With reference to FIG. 5, radiation from the optical source 17 passes through the sample cell and is received by the measuring element 38. The output 42 from measuring element 38 and output 44 from reference element 36 are differentially added and amplified by amplifier 46. The amplified output 48 is AC coupled by capacitor 50 and resistance 52 to linear amplifier 54. The AC coupling is a high pass filter that attenuates any changes in the signal output 48 slower than the lowest desired respiration rate, suitably 3 breaths per minute. The output 56 of amplifier 54 is input to a 3 hertz low-pass filter made up of resistance 58 and capacitor 60. The circuitry through this stage is on the printed circuit board 37 in the sensor assembly. Cable 53 interconnects the sensor assembly circuits with indicator 57 that contains a power source (not shown) and circuitry to receive the output 62.

The output 62 is connected to voltage threshold comparator 64 having a 1.0 V reference that is designed to detect a negative signal equivalent to 0.5% carbon dioxide. When the input signal to the comparator is large enough, the comparator output 66 initiates pulse generator 68 that generates a 0.2 second output pulse 69. The pulse is passed by diode 70 and is amplified by amplifier 72 to light green LED 74. The pulse also passes diode 76 to CMOS oscillator 78 that sounds piezoelectric tone generator 80. The LED blinks on and the buzzer sounds with every exhalation giving a positive indication of respiration.

Timer 81 is a resettable binary counter that is reset by the pulse 69 from pulse generator 68. If a signal is not generated from the pulse generator within a predetermined reset time, the timer generates a 0.2 millisecond pulse to $R_1$ and $R_2$ latching high the output $\overline{Q_2}$ output 84 from switch $S_2$ and $\overline{Q_1}$ output 86 from switch $S_1$ of flip-flop switch 82 to light red LED 88 and actuate tone generator 80, giving a continuous positive alarm of respiration failure. The tone generator can be silenced by closing reset switch 89; diode 90 isolates the reset switch from resetting $\overline{Q_1}$ through $R_1$, so the red LED remains lit when the audible alarm is silenced.

We claim:

1. A respiration monitor for attachment to an endotracheal tube comprising
    a tubular member adapted to receive respired air from an endotracheal tube and having diametrically opposed planar windows substantially transparent to infrared radiation;
    an infrared analyzer comprising a source means for producing an unmodulated beam of infrared radiation passing through the planar windows and respired air, and a detector means to receive infrared radiation after passage through said windows and respired air and to generate an output signal in response to the presence of $CO_2$ in each expiration;
    the detector means comprising a chamber having an infrared transparent window, a first and second solid state infrared detector element within the chamber, and an infrared opaque shield on the outside surface of the window interposed between the source and the second solid state element, said first element being a measuring element and said second element being a reference element;
    means for detecting the time between signals generated by said detector;
    and alarm means responsive to a predetermined delay between said signals.

2. A respiration monitor according to claim 1 having matched thermopile elements.

3. A respiration monitor according to claim 2 in which the chamber is in thermal contact with a heat sink.

4. A respiration monitor according to claim 3 in which the chamber walls are metal and are in contact with a copper sheath covered by thermal insulation.

5. A respiration monitor according to claim 1 in which the detector is in thermal contact with a heat sink.

6. A respiration monitor according to claim 1 having means to filter out signals at a frequency below that of a predetermined respiration rate.

* * * * *